United States Patent [19]

Gericke et al.

[11] Patent Number: 5,700,839
[45] Date of Patent: Dec. 23, 1997

[54] ALKYL-5-METHYLSULFONYLBENZOYL-GUANIDINE DERIVATIVES

[75] Inventors: Rolf Gericke, Seeheim; Dieter Dorsch, Ober-Ramstadt; Manfred Baumgarth, Darmstadt; Klaus-Otto Minck, Ober-Ramstadt; Norbert Beier, Reinheim, all of Germany

[73] Assignee: Merck Patent Gesellschaft mit Beschrankter Haftung, Darmstadt, Germany

[21] Appl. No.: 546,570

[22] Filed: Oct. 20, 1995

[30] Foreign Application Priority Data

Oct. 22, 1994 [DE] Germany .................. 44 37 874.2

[51] Int. Cl.$^6$ ............... A61K 31/165; C07C 235/50; C07C 231/02; C07C 231/12
[52] U.S. Cl. ............... 514/618; 514/821; 514/866; 564/133; 564/139; 564/144; 564/162
[58] Field of Search ................... 514/618, 821, 514/866; 564/162, 133, 139, 144

[56] References Cited

FOREIGN PATENT DOCUMENTS 0416499  3/1991  European Pat. Off. .
0556673  8/1993  European Pat. Off. .

*Primary Examiner*—Peter O'Sullivan
*Attorney, Agent, or Firm*—Millen, White, Zelano, & Branigan, P.C.

[57] ABSTRACT

Benzoylguanidines of the formula I

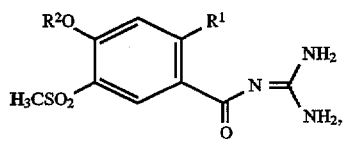

wherein $R^1$ and $R^2$ have the meanings indicated herein, and their physiologically acceptable salts, show anti-arrhythmic properties and act as inhibitors of the cellular $NA^+/H^+$ antiporter.

11 Claims, No Drawings

ALKYL-5-METHYLSULFONYLBENZOYL-GUANIDINE DERIVATIVES

The invention relates to benzoylguanidine derivatives of the formula I

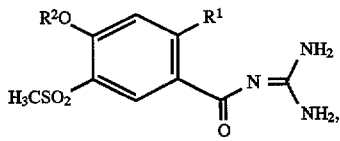

wherein
$R^1$ is methyl or ethyl and
$R^2$ is H, a straight-chain or branched $C_1$–$C_6$-alkyl- or $C_2$–$C_6$-alkenyl-radical, $C_3$–$C_7$-cycloalkyl, benzyl or phenyl which is unsubstituted or mono-, di- or trisubstituted by methyl, methoxy, amino, F, Cl, Br and/or $CF_3$,
and their physiologically acceptable salts.

An object of the invention is finding novel compounds having useful properties, in particular those which can be used for the production of medicaments.

Upon further study of the specification and appended claims, further objects and advantages of this invention will become apparent to those skilled in the art.

It has been found that the compounds of the formula I and their physiologically acceptable salts have useful pharmacological properties combined with good tolerability.

The novel compounds are inhibitors of the cellular $Na^+/H^+$ antiporter, i.e., active compounds which inhibit the $Na^+/H^+$ exchange mechanism of the cells (Düsing et al., Med. Klin. 87, 378–384 (1992)) and are thus good antiarrythmics. They are particularly suitable for the treatment of arrhythmias which occur as a result of oxygen deficiency.

The best known active compound of the acylguanidine group is amiloride. This substance, however, primarily shows a hypotensive and saluretic action, which is undesired, in particular in the treatment of cardiac arrhythmias, while the antiarrhythmic properties are only very poorly pronounced.

Moreover, structurally similar compounds are known, for example, from EP 04 16 499.

The invention relates to compounds of the formula I and their physiologically acceptable salts.

The substances according to the invention of the present application show a good cardioprotective action and are therefore particularly suitable for infarct treatment, infarct prophylaxis and for the treatment of angina pectoris. The substances also counteract all pathological hypoxic and ischaemic damage, so that the diseases caused primarily or secondarily thereby can be treated. The active compounds are also highly suitable for preventive applications.

On account of the protective effects of these substances in pathological hypoxic or ischaemic situations, other application possibilities result therefrom in surgical interventions for the protection of temporarily undersupplied organs, in organ transplantation for the protection of the removed organs, in angioplastic vascular or cardiac interventions, in ischaemias of the nervous system, in the therapy of states of shock and for the preventive treatment of essential hypertension.

In addition, the compounds can also be used as therapeutics in disorders caused by cell proliferation, such as arteriosclerosis, diabetic late complications, oncoses, fibrotic disorders, in particular of the lungs, liver and kidneys, as well as organ hypertrophies and hyperplasias. The substances are moreover suitable for diagnostic application for the identification of diseases which are accompanied by an increased activity of the $Na^+/H^+$ antiporter, e.g. in erythrocytes, platelets or leukocytes.

The effects of the compounds can be determined with the aid of methods known per se, such as are indicated by N. Escobales and J. Figueroa in J. Membrane Biol. 120, 41–49 (1991) or by L. Counillon, W. Scholz, H. J. Lang and J. Pouysségur in Mol. Pharmacol. 44, 1041–1045 (1993).

Suitable experimental animals are, for example, mice, rats, guinea-pigs, dogs, cats, monkeys or pigs.

The compounds can therefore be used as pharmaceutically active compounds in human and veterinary medicine. They can also be used as intermediates for the production of other pharmaceutically active compounds.

$R^2$ is preferably methyl, ethyl or phenyl, but also preferably benzyl or cycloalkyl having 3, 5 or 6 C atoms, i.e. in particular cyclopropyl, cyclopentyl or cyclohexyl. If $R^2$ is phenyl, it is preferably unsubstituted or monosubstituted by fluorine or chlorine.

Accordingly, the invention in particular relates to those compounds of the formula I in which at least one of the radicals mentioned has one of the preferred meanings indicated above. Some preferred compounds of the formula I are:

N-diaminomethylene-2-methyl-4-phenoxy-5-methylsulfonylbenzamide;

N-diaminomethylene-2-ethyl-4-phenoxy-5-methylsulfonylbenzamide;

N-diaminomethylene-2-methyl-4-hydroxy-5-methylsulfonylbenzamide;

N-diaminomethylene-2-ethyl-4-hydroxy-5-methylsulfonylbenzamide;

N-diaminomethylene-2-methyl-4-benzyloxy-5-methylsulfonylbenzamide;

N-diaminomethylene-2-ethyl-4-benzyloxy-5-methylsulfonylbenzamide;

N-diaminomethylene-2-methyl-4-methoxy-5-methylsulfonylbenzamide;

N-diaminomethylene-2-ethyl-4-methoxy-5-methylsulfonylbenzamide;

N-diaminomethylene-2-ethyl-4-cyclopropyloxy-5-methylsulfonylbenzamide;

N-diaminomethylene-2-ethyl-4-cyclopentyloxy-5-methylsulfonylbenzamide;

N-diaminomethylene-2-ethyl-4-cyclohexyloxy-5-methylsulfonylbenzamide.

The invention also relates to a process for preparing the compounds of the formula I according to claim 1, and also their salts, characterized in that a compound of the formula II

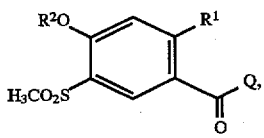

wherein $R^1$ and $R^2$ have the meanings indicated above and Q is Cl, Br, OA, O—CO—A, O—CO—Ph, OH or another reactive esterified OH group or leaving group which can be easily nucleophilically substituted and A is alkyl having 1–6 C atoms, is reacted with guanidine, or in that a benzoylguanidine of the formula III

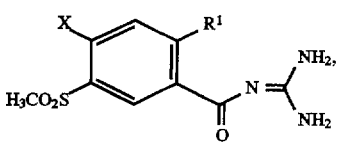

wherein $R^1$ has the meanings indicated above, and
X is F, Cl, Br, I or another suitable leaving group, is reacted with an alcohol or phenol of the formula IV $R^2$—OH    IV wherein
$R^2$ has the meaning indicated,
if appropriate after prior conversion to an alkoxide,
or in that an alcohol (phenol) of the formula I wherein $R^2$=H and $R^1$ has the meaning indicated is reacted with a compound of the formula $R^2$-X wherein $R^2$ and X have the meanings indicated,
or in that a compound which otherwise corresponds to the formula I, but which instead of one or more hydrogen atoms contains one or more reducible groups and/or one or more additional C-C and/or C-N bonds, is treated with a reducing agent,
or in that a compound which otherwise corresponds to the formula I, but which instead of one or more hydrogen atoms contains one or more solvolysable groups, is treated with a solvolysing agent
and/or in that a base of the formula I which is obtained is converted into one of its salts by treating with an acid.

The compounds of the formula I are otherwise prepared by methods known per se, as are described in the literature (e.g. in the standard works such as Houben-Weyl, Methoden der organischen Chemie (Methods of organic chemistry), Georg-Thieme-Verlag, Stuttgart; Organic Reactions, John Wiley & Sons, Inc., New York; and in the patent application indicated above), namely under reaction conditions which are known and suitable for the reactions mentioned. In this case, use can also be made of variants which are known per se but are not mentioned in greater detail here.

If desired, the starting substances can also be formed in situ in such a way that they are not isolated from the reaction mixture, but immediately reacted further to give the compounds of the formula I.

Preferably, compounds of the formula I are prepared by reacting an activated carboxylic acid derivative of the formula II, where Q is particularly preferably Cl or —O—$CH_3$, with guanidine. Particularly suitable reaction variants are also those in which the free carboxylic acid II (Q=OH) is reacted in a manner known per se to give the respective activated derivative and this is then reacted directly, without intermediate isolation, with guanidine. Methods in which intermediate isolation is unnecessary are, for example, activation with carbonyldiimidazole, dicyclohexylcarbodiimide or the Mukayama variant (Angew. Chem. 91, 788–812 (1979)).

Generally, the carboxylic acids and carboxylic acid derivatives of the formula II are known. They are prepared, in particular, by reacting an appropriate 2-alkyl-4-halo-5-methylsulfonylbenzoic acid derivative with an alkoxide or a phenoxide which can be derived from an alcohol or phenol of the formula IV.

The reaction is carried out in analogy to the reaction of the compounds III and IV. It is described below.

The reaction of a reactive carboxylic acid derivative of the formula II with guanidine is carried out in a manner known per se, preferably in a protic or aprotic polar or non-polar inert organic solvent.

Suitable solvents for the reaction of the compounds III and IV are mentioned below. Particularly preferred solvents are, however, methanol, THF, dimethoxyethane, dioxane or mixtures which can be prepared therefrom, as well as water. Suitable reaction temperatures are, for example, temperatures from 20° C. to the boiling point of the solvent. The reaction times are preferably from 5 minutes to 12 hours. It is expedient to employ an acid scavenger in the reaction. Those suitable for this purpose are any types of bases which do not interfere with the reaction itself. Particularly suitable, however, is the use of inorganic bases such as potassium carbonate or of organic bases such as triethylamine or pyridine or else an excess of the guanidine.

Compounds of the formula I can also be prepared by reacting a benzoylguanidine of the formula III with a compound of the formula IV. The starting substances of the formula III can be prepared by reaction of appropriately substituted benzoic acids or reactive acid derivatives which can be derived therefrom, such as acid halides, esters or anhydrides, with guanidine under reaction conditions as are known per se and generally customary for amide preparation. Particularly suitable reaction variants are, in turn, those as have previously been indicated for the reaction of compound II with guanidine.

The preparation of the compound II and the reaction of the compound III with a compound of the formula IV are carried out in a manner known per se, preferably in a protic or aprotic polar inert organic solvent.

In the preparation of II or in the reaction of III with IV, it is also expedient to work in the presence of a base or with an excess of the basic component. Suitable bases are preferably, for example, alkali metal or alkaline earth metal hydroxides, carbonates or alkoxides, or organic bases such as triethylamine or pyridine which are also used in an excess and can then simultaneously serve as solvents.

Suitable inert solvents are particularly alcohols such as methanol, ethanol, isopropanol, n-butanol or tert-butanol; ethers such as diethyl ether, diisopropyl ether, tetrahydrofuran (THF) or dioxane; glycol ethers such as ethylene glycol monomethyl ether or monoethyl ether (methyl glycol or ethyl glycol), ethylene glycol dimethyl ether (diglyme); ketones such as acetone or butanone; nitriles such as acetonitrile; nitro compounds such as nitromethane or nitrobenzene; esters such as ethyl acetate; amides such as hexamethylphosphoramide; sulfoxides such as dimethyl sulfoxide (DMSO); chlorinated hydrocarbons such as dichloromethane, chloroform, trichloroethylene, 1,2-dichloroethane or carbon tetrachloride; or hydrocarbons such as benzene, toluene or xylene. Mixtures of these solvents with one another are additionally suitable.

The compounds of the formula I can also be obtained by setting them free from their functional derivatives by solvolysis, in particular hydrolysis, or by hydrogenolysis.

Preferred starting substances for the solvolysis or hydrogenolysis are those which otherwise correspond to the formula I, but instead of one or more free amino and/or hydroxyl groups contain corresponding protected amino and/or hydroxyl groups, preferably those which, instead of an H atom which is bonded to an N atom, carry an amino protective group, in particular those which instead of an HN group carry an R'-N group wherein R' is an amino protective group, and/or those which instead of the H atom of a hydroxyl group carry a hydroxyl protective group, e.g. those which correspond to the formula I but instead of an OH group carry an OR" group wherein R" is a hydroxyl protective group.

Two or more identical or different protected amino and/or hydroxyl groups can also be present in the molecule of the starting substance. If the protective groups present are different from one another, in many cases they can be removed selectively.

The expression "amino protective group" is generally known and relates to groups which are suitable for protecting (for blocking) an amino group from chemical reactions, but which are easily removable after the desired chemical reaction has been carried out in another position of the molecule. Typical groups of this type are particularly unsubstituted or substituted acyl, aryl (e.g. 2,4-dinitrophenyl (DNP)), aralkoxymethyl (e.g. benzyloxymethyl (BOM)) or aralkyl groups (e.g. benzyl, 4-nitrobenzyl, triphenylmethyl). As the amino protective groups are removed after the desired reaction (or reaction sequence) their nature and size is otherwise uncritical; however those having 1–20, in particular 1–8, C atoms are preferred. The expression "acyl group" is to be interpreted in the widest sense in connection with the present process. It includes acyl groups derived from aliphatic, araliphatic, aromatic or heterocyclic carboxylic acids or sulfonic acids and also, in particular, alkoxycarbonyl, aryloxycarbonyl and especially aralkoxycarbonyl groups. Examples of acyl groups of this type are alkanoyl such as acetyl, propionyl, butyryl; aralkanoyl such as phenylacetyl; aroyl such as benzoyl or tolyl; aryloxyalkanoyl such as phenoxyacetyl; alkoxycarbonyl such as methoxycarbonyl, ethoxycarbonyl, 2,2,2-trichloroethoxycarbonyl, isopropoxycarbonyl, tert-butoxycarbonyl (BOC), 2-iodoethoxycarbonyl; aralkyloxycarbonyl such as benzyloxycarbonyl (CBZ), 4-methoxybenzyloxycarbonyl and 9-fluorenylmethoxycarbonyl (FMOC). Preferred amino protective groups are BOC, DNP and BOM, and also CBZ, benzyl and acetyl.

The expression "hydroxyl protective group" is also generally known and relates to groups which are suitable for protecting a hydroxyl group from chemical reactions, but which are easily removable after the desired chemical reaction has been carried out in another position of the molecule. Typical groups of this type are the abovementioned unsubstituted or substituted aryl, aralkyl or acyl groups, and also alkyl groups. The nature and size of the hydroxyl protective groups is not critical, as they are removed after the desired chemical reaction or reaction sequence; groups having 1–20, in particular 1–10, C atoms are preferred. Examples of hydroxyl protective groups are, inter alia, tert-butyl, benzyl, p-nitrobenzoyl, p-toluenesulfonyl and acetyl, benzyl and acetyl being particularly preferred.

The functional derivatives of the compounds of the formula I to be used as starting substances can be prepared by customary methods, as are described, for example, in the standard works and patent applications mentioned, e.g. by reaction of compounds which correspond to the formulae II and III, but where at least one of these compounds contains a protective group instead of an H atom.

The liberation of the compounds of the formula I from their functional derivatives takes place, depending on the protective group used, e.g. with strong acids, expediently with trifluoroacetic acid or perchloric acid, but also with other strong inorganic acids such as hydrochloric acid or sulfuric acid, strong organic carboxylic acids such as trichloroacetic acid, or sulfonic acids such as benzene- or p-toluenesulfonic acid. The presence of an additional inert solvent is possible, but not always necessary.

Suitable inert solvents are preferably organic, for example carboxylic, acids such as acetic acid, ethers such as tetrahydrofuran (THF) or dioxane, amides such as dimethylformamide (DMF), halogenated hydrocarbons such as dichloromethane, and also alcohols such as methanol, ethanol or isopropanol, and also water. Mixtures of the abovementioned solvents are also possible. Trifluoroacetic acid is preferably used in an excess without addition of a further solvent; perchloric acid is used in the form of a mixture of acetic acid and 70% perchloric acid in the ratio 9:1. The reaction temperatures for the cleavage are expediently from approximately 0° C. to approximately 50° C.; the reaction is preferably carried out at about from 15°–30° C. (room temperature).

The BOC group can be preferably removed, for example, using 40% trifluoroacetic acid in dichloromethane or using approximately. 3 to 5N HCl in dioxane at 15°–60° C.; the FMOC group using an approximately 5–20% solution of dimethylamine, diethylamine or piperidine in DMF at 15°–50° C. Removal of the DNP group is carried out, for example, also using an approximately 3–10% solution of 2-mercaptoethanol in DMF/water at 15°–30° C.

Hydrogenolytically removable protective groups (e.g. BOM, CBZ or benzyl) can be removed, for example, by treating with hydrogen in the presence of a catalyst (e.g. a noble metal catalyst such as palladium, expediently on a support such as carbon). Suitable solvents in this case are those indicated above, in particular, for example, alcohols such as methanol or ethanol or amides such as DMF. Generally, the hydrogenolysis is carried out at temperatures from approximately 0°–100° C. and pressures from approximately 1–200 bar, preferably at 20°–30° C. and 1–10 bar. Hydrogenolysis of the CBZ group takes place readily, for example, on 5–10% Pd-C in methanol at 20°–30° C.

A base of the formula I can also be converted into the associated acid addition salt using an acid. For this reaction, possible acids are those which give physiologically acceptable salts. Inorganic acids can thus be used, e.g. sulfuric acid, nitric acid, halohydric acids such as hydrochloric acid or hydrobromic acid, phosphoric acids such as orthophosphoric acid, sulfamic acid, and also organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids and laurylsulfuric acid.

The compounds may be used as pharmaceutical agents in a manner analogous to amiloride and other known acylguanidine compounds, but exhibiting the advantages described herein, e.g. inhibition of the cellular $Na^+/H^+$ exchange mechanism and activity in the treatment and prevention of disturbances of the cardiac rhythm. As intermediates, the compounds may be used to prepare pharmaceutically active compounds using synthetic methods analogous to those known in the art.

The compounds of the formula I and their physiologically acceptable salts can be used for the production of pharmaceutical preparations, in particular by non-chemical routes. In this context, they can be brought into a suitable dose form together with at least one solid, liquid and/or semi-liquid excipient or auxiliary and, if appropriate, in combination with one or more other active compounds.

The invention also relates to compositions, in particular pharmaceutical preparations, containing at least one compound of the formula I and/or one of its physiologically acceptable salts.

These preparations can be used as medicaments in human or veterinary medicine. Possible excipients are organic or inorganic substances which are suitable for enteral (e.g. oral) or parenteral administration or topical application and do not react with the novel compounds, for example water, vegetable oils, benzyl alcohols, polyethylene glycols, glycerol triacetate, gelatin, carbohydrates such as lactose or starch, magnesium stearate, talc, lanolin and petroleum jelly. Tablets, coated tablets, capsules, syrups, juices or drops, in particular, are used for oral administration, suppositories for rectal administration, solutions, preferably oily or aqueous solutions, and also suspensions, emulsions or implants, for parenteral administration, and ointments, creams, pastes, lotions, gels, sprays, foams, aerosols, solutions (e.g. solutions in alcohols such as ethanol or isopropanol, acetonitrile, DMF, dimethylacetamide, 1,2-propanediol or mixtures thereof with one another and/or with water) or powders for topical application. The novel compounds can also be lyophilized and the lyophilizates obtained used, for example, for the production of injection preparations.

Liposomal preparations are also suitable, in particular for topical application. The preparations indicated can be sterilized and/or contain auxiliaries such as lubricants, preservatives, stabilizers and/or wetting agents, emulsifiers, salts for affecting the osmotic pressure, buffer substances, colorants, flavorings and/or aromatic substances. If desired, they can also contain one or more other active compounds, e.g. one or more vitamins.

The compounds of the formula I and their physiologically acceptable salts can be administered to humans or animals, in particular mammals such as monkeys, dogs, cats, rats or mice, and used in the therapeutic treatment of the human or animal body and also in the control of diseases, in particular in the therapy and/or prophylaxis of disorders of the cardiovascular system. They are therefore suitable for the treatment of arrhythmias, in particular if these are caused by oxygen deficiency, of angina pectoris, infarcts, ischaemias of the nervous system such as, for example, stroke or cerebral oedema, of states of shock and for preventive treatment, for example, preventive treatment of the above disorders.

The substances can also be employed as therapeutics in disorders in which cell proliferation plays a role, such as arteriosclerosis, diabetic late complications, oncoses, fibroses and organ hypertrophies and hyperplasias, in particular in disorders of the prostate.

In this case, generally, the substances according to the invention are administered in analogy to known antiarrhythmics, e.g. aprindine, preferably in doses from approximately 0.01–5 mg, in particular from 0.02–0.5 mg per unit dose. The daily dose is preferably from approximately 0.0001–0.1, in particular from 0.0003–0.01, mg/kg of body weight. The specific dose for each intended patient, however, depends on all sorts of factors, for example on the efficacy of the specific compound employed, on the age, body weight, the general state of health, sex, on the diet, on the time and route of administration, and on the excretion rate, pharmaceutical combination and severity of the particular disorder to which the therapy applies. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of the corresponding application, German Application P4437874.02, are hereby incorporated by reference.

In the following examples "customary working up" means:

If necessary, water is added, the mixture is extracted with an organic solvent such as ethyl acetate, the organic phase is separated off, dried over sodium sulfate, filtered and evaporated and the residue is purified by chromatography and/or crystallization.

EXAMPLE 1

A solution of 1.4 g of methyl 2-methyl-4-ethoxy-5-methylsulfonylbenzoate (obtainable by reaction of 2-methyl-4-chloro-5-methylsulfonylbenzoic acid with sodium ethoxide and subsequent esterification) and 1.5 g of guanidine in 50 ml of methanol is boiled for five hours and the solvent is then removed. The residue is treated with water, and the crystallizate which remains is filtered off with suction and treated with dilute sodium hydroxide solution. The solid residue is filtered off and recrystallized from ethanol, and N-diaminomethylene-2-methyl-4-ethoxy-5-methylsulfonylbenzamide is obtained, m.p. 201°–203°.

Analogously, reaction of guanidine with methyl 2-ethyl-4-ethoxy-5-methylsulfonylbenzoate gives N-diaminomethylene-2-ethyl-4-ethoxy-5-methylsulfonylbenzamide;

with methyl 2-methyl-4-isopropoxy-5-methylsulfonylbenzoate gives N-diaminomethylene-2-methyl-4-isopropoxy-5-methylsulfonylbenzamide; m.p. 185°–188°;

with methyl 2-methyl-4-tert-butoxy-5-methylsulfonylbenzoate gives N-diaminomethylene-2-methyl-4-tert-butoxy-5-methylsulfonylbenzamide; m.p. 205°–207°;

with methyl 2-methyl-4-butoxy-5-methylsulfonylbenzoate gives N-diaminomethylene-2-methyl-4-butoxy-5-methylenesulfonylbenzamide;

with methyl 2-methyl-4-(2-butoxy)-5-methylsulfonylbenzoate gives N-diaminomethylene-2-methyl-4-(2-butoxy)-5-methylsulfonylbenzamide;

with methyl 2-methyl-4-cyclopentoxy-5-methylsulfonylbenzoate gives N-diaminomethylene-2-methyl-4-cyclopentoxy-5-methylsulfonylbenzamide; m.p. 238°–241°;

with methyl 2-methyl-4-(2-pentoxy)-5-methylsulfonylbenzoate gives N-diaminomethylene-2-methyl-4-(2-pentoxy)-5-methylsulfonylbenzamide;

with methyl 2-methyl-4-(3-pentoxy)-5-methylsulfonylbenzoate gives N-diaminomethylene-2-methyl-4-(3-pentoxy)-5-methylsulfonylbenzamide;

with methyl 2-methyl-4-cyclohexyloxy-5-methylsulfonylbenzoate gives N-diaminomethylene-2-methyl-4-cyclohexyloxy-5-methylsulfonylbenzamide; m.p. 224°–226°;

with methyl 2-methyl-4-cyclopropoxy-5-methylsulfonylbenzoate gives N-diaminomethylene-2-methyl-4-cyclopropoxy-5-methylsulfonylbenzamide;

with methyl 2-ethyl-4-methoxy-5-methylsulfonylbenzoate gives N-diaminomethylene-2-ethyl-4-methoxy-5-methylsulfonylbenzamide; m.p. 192°–195°;

with methyl 2-ethyl-4-isopropoxy-5-methylsulfonylbenzoate gives N-diaminomethylene-2-ethyl-4-isopropoxy-5-methylsulfonylbenzamide;
with methyl 2-ethyl-4-propoxy-5-methylsulfonylbenzoate gives N-diaminomethylene-2-ethyl-4-propoxy-5-methylsulfonylbenzamide;
with methyl 2-ethyl-4-butoxy-5-methylsulfonylbenzoate gives N-diaminomethylene-2-ethyl-4-butoxy-5-methylsulfonylbenzamide;
with methyl 2-ethyl-4-(2-butoxy)-5-methylsulfonylbenzoate gives N-diaminomethylene-2-ethyl-4-(2-butoxy)-5-methylsulfonylbenzamide;
with methyl 2-ethyl-4-tert-butoxy-5-methylsulfonylbenzoate gives N-diaminomethylene-2-methyl-4-tert-butoxy-5-methylsulfonylbenzamide;
with methyl 2-ethyl-4-pentoxy-5-methylsulfonylbenzoate gives N-diaminomethylene-2-ethyl-4-pentoxy-5-methylsulfonylbenzamide;
with methyl 2-ethyl-4-(2-pentoxy)-5-methylsulfonylbenzoate gives N-diaminomethylene-2-ethyl-4-(2-pentoxy)-5-methylsulfonylbenzamide;
with methyl 2-ethyl-4-(3-pentoxy)-5-methylsulfonylbenzoate gives N-diaminomethylene-2-ethyl-4-(3-pentoxy)-5-methylsulfonylbenzamide;
with methyl 2-ethyl-4-cyclopropoxy-5-methylsulfonylbenzoate gives N-diaminomethylene-2-ethyl-4-cyclopropoxy-5-methylsulfonylbenzamide;
with methyl 2-ethyl-4-cyclopentoxy-5-methylsulfonylbenzoate gives N-diaminomethylene-2-ethyl-4-cyclopentoxy-5-methylsulfonylbenzamide;
with methyl 2-ethyl-4-cyclohexyloxy-5-methylsulfonylbenzoate gives N-diaminomethylene-2-ethyl-4-cyclohexyloxy-5-methylsulfonylbenzamide.

EXAMPLE 2

3.0 g of N-diaminomethylene-2-ethyl-4-fluoro-5-methytsulfonylbenzamide (obtainable by reaction of methyl 2-ethyl-4-fluoro-5-methylsulfonylbenzoate with guanidine), and 1.5 g of sodium methoxide are boiled in 25 ml of methanol for 16 hours. Customary working up gives N-diaminomethylene-2-ethyl-4-methoxy-5-methylsulfonylbenzamide, m.p. 192°–195°.

Analogously, reaction of sodium methoxide
with N-diaminomethylene-2-methyl-4-chloro-5-methylsulfonylbenzamide gives N-diaminomethylene-2-methyl-4-methoxy-5-methylsulfonylbenzamide, m.p. 189°–190°;

EXAMPLE 3

700 mg of N-diaminomethylene-2-ethyl-4-methoxy-methylsulfonylbenzamide (obtainable according to Ex. 2) are suspended in 50 ml of water and treated with 1.8 mi of 1N HCl with stirring. After filtration and lyophilization, N-diaminomethylene-2-ethyl-4-methoxy-5-methylsulfonylbenzamide hydrochloride, m.p. 217°–220°, is obtained.

Analogously, the free base gives
N-diaminomethylene-2-methyl-4-ethoxy-5-methylsulfonylbenzamide,hydrochloride, m.p. 218°–219°;
N-diaminomethylene-2-methyl-4-isopropoxy-methylsulfonylbenzamide, hydrochloride, m.p. 216°–220°;
N-diaminomethylene-2-methyl-4-cyclopentoxy-5-methylsulfonylbenzamide, hydrochloride, m.p. >250°;
N-diaminomethylene-2-methyl-4-cyclohexyloxy-5-methylsulfonylbenzamide, hydrochloride, m.p. 185°–187°;
N-diaminomethylene-2-methyl-4-benzyloxy-5-methylsulfonyl-benzamide,hydrochloride, amorphous.
N-diaminomethylene-2-methyl-4-methoxy-5-methylsulfonylbenzamide, hydrochloride, amorphous.

EXAMPLE 4

1.8 g of 2-methyl-4-phenoxy-5-methylsulfonylbenzoic acid (obtainable by reaction of 2-methyl-4-chloro-5-methylsulfonylbenzoic acid with sodium phenoxide at 180°) are boiled for three hours together with 25 ml of $SOCl_2$. The clear solution is concentrated and the residue is dissolved in 20 ml of ethylene glycol dimethyl ether. This reaction mixture is slowly added at room temperature to 2.5 g of guanidine, dissolved in 30 ml of ethylene glycol dimethyl ether, and the mixture is subsequently stirred for three hours. The solution is then concentrated to one half, treated with 50 ml of water, acidified and worked up in the customary manner. N-Diaminomethylene-2-methyl-4-phenoxy-5-methylsulfonylbenzamide, m.p. 248°–250°, is obtained.

After suspending the base in 50 ml of water and treating it with 1.8 ml of 1N HCl with stirring, N-diaminomethylene-2-methyl-4-phenoxy-5-methylsulfonylbenzamide hydrochloride, m.p. >250°, is obtained following filtration and lyophilization.

EXAMPLE 5

Analogously to Example 4, reaction of 2-methyl-4-(2-chlorophenoxy)-5-methylsulfonylbenzoic acid (obtainable by reaction of 2-methyl-4-chloro-5-methylsulfonylbenzoic acid with sodium 2-chlorophenoxide at 180°) with $SOCl_2$ and subsequently with guanidine gives N-diaminomethylene-2-methyl-4-(2-chlorophenoxy)-5-methylsulfonylbenzamide, m.p. 188°–191°.

Analogously,
2-methyl-4-(3-chlorophenoxy)-5-methylsulfonylbenzoic acid gives N-diaminomethylene-2-methyl-4-(3-chlorophenoxy)-5-methylsulfonylbenzamide, m.p. 205°–207°;
2-methyl-4-(4-chlorophenoxy)-5-methylsulfonylbenzoic acid gives N-diaminomethylene-2-methyl-4-(4-chlorophenoxy)-5-methylsulfonylbenzamide, m.p. 219°–221°;
2-methyl-4-(2,4-dichlorophenoxy)-5-methylsulfonylbenzoic acid gives N-diaminomethylene-2-methyl-4-(2,4-dichlorophenoxy)-5-methylsulfonylbenzamide;
2-methyl-4-(2-fluorophenoxy)-5-methylsulfonylbenzoic acid gives N-diaminomethylene-2-methyl-4-(2-fluorophenoxy)-5-methylsulfonylbenzamide;
2-methyl-4-(3-fluorophenoxy)-5-methylsulfonylbenzoic acid gives N-diaminomethylene-2-methyl-4-(3-fluorophenoxy)-5-methylsulfonylbenzamide;
2-methyl-4-(4-fluorophenoxy)-5-methylsulfonylbenzoic acid gives N-diaminomethylene-2-methyl-4-(4-fluorophenoxy)-5-methylsulfonylbenzamide;
2-methyl-4-(2,4-difluorophenoxy)-5-methylsulfonylbenzoic acid gives N-diaminomethylene-2-methyl-4-(2,4-difluorophenoxy)-5-methylsulfonylbenzamide;
2-methyl-4-benzyloxy-5-methylsulfonylbenzoic acid gives N-diaminomethylene-2-methyl-4-benzyloxy-5-methylsulfonylbenzamide, m.p. 212°–217°;
2-methyl-4-(3-methoxyphenoxy)-5-methylsulfonylbenzoic acid gives N-diaminomethylene-2-methyl-4-(3-methoxyphenoxy)-5-methylsulfonylbenzamide;
2-methyl-4-(4-methoxyphenoxy)-5-methylsulfonylbenzoic acid gives N-diaminomethylene-2-methyl-4-(4-methoxyphenoxy)-5-methylsulfonylbenzamide;
2-methyl-4-(2,4-dimethoxyphenoxy)-5-methylsulfonylbenzoic acid gives N-diaminomethylene-2- methyl-4-(2,4-dimethoxyphenoxy)-5-methylsulfonylbenzamide;

2-methyl-4-(2-methoxyphenoxy)-5-methylsulfonylbenzoic acid gives N-diaminomethylene-2-methyl-4-(2-methoxyphenoxy)-5-methylsulfonylbenzamide;

2-methyl-4-(3-trifluoromethylphenoxy)-5-methylsulfonylbenzoic acid gives N-diaminomethylene-2-methyl-4-(3-trifluoromethylphenoxy)-5-methylsulfonylbenzamide;

2-methyl-4-(4-trifluoromethylphenoxy)-5-methylsulfonylbenzoic acid gives N-diaminomethylene-2-methyl-4-(4-trifluoromethylphenoxy)-5-methylsulfonylbenzamide;

2-methyl-4-(2-trifluoromethylphenoxy)-5-methylsulfonylbenzoic acid gives N-diaminomethytene-2-methyl-4-(2-trifluoromethylphenoxy)-5-methylsulfonylbenzamide;

2-methyl-4-(3-methylphenoxy)-5-methylsulfonylbenzoic acid gives N-diaminomethylene-2-methyl-4-(3-methylphenoxy)-5-methylsulfonylbenzamide;

2-methyl-4-(4-methylphenoxy)-5-methylsulfonylbenzoic acid gives N-diaminomethylene-2-methyl-4-(4-methylphenoxy)-5-methylsulfonylbenzamide;

2-methyl-4-(2,4-dimethylphenoxy)-5-methylsulfonylbenzoic acid gives N-diaminomethylene-2-methyl-4-(2,4-dimethylphenoxy)-5-methylsulfonylbenzamide;

2-methyl-4-(2-methylphenoxy)-5-methylsulfonylbenzoic acid gives N-diaminomethylene-2-methyl-4-(2-methylphenoxy)-5-methylsulfonylbenzamide.

EXAMPLE 6

Analogously to Example 4, reaction of 2-ethyl-4-(2-chlorophenoxy)-5-methylsulfonylbenzoic acid (obtainable by reaction of 2-ethyl-4-chloro-5-methylsulfonylbenzoic acid with sodium 2-chlorophenoxide at 180°) with $SOCl_2$ and subsequently with guanidine gives N-diaminomethylene-2-ethyl-4-(2-chlorophenoxy)-5-methylsulfonylbenzamide.

Analogously,
2-ethyl-4-phenoxy-5-methylsulfonylbenzoic acid gives N-diaminomethylene-2-ethyl-4-phenoxy-5-methylsulfonylbenzamide;

2-ethyl-4-(3-chlorophenoxy)-5-methylsulfonylbenzoic acid gives N-diaminomethylene-2-ethyl-4-(3-chlorophenoxy)-5-methylsulfonylbenzamide;

2-ethyl-4-(4-chlorophenoxy)-5-methylsulfonylbenzoic acid gives N-diaminomethylene-2-ethyl-4-(4-chlorophenoxy)-5-methylsulfonylbenzamide;

2-ethyl-4-(2,4-dichlorophenoxy)-5-methylsulfonylbenzoic acid gives N-diaminomethylene-2-ethyl-4-(2,4-dichlorophenoxy)-5-methylsulfonylbenzamide;

2-ethyl-4-(2-fluorophenoxy)-5-methylsulfonylbenzoic acid gives N-diaminomethylene-2-ethyl-4-(2-fluorophenoxy)-5-methylsulfonylbenzamide;

2-ethyl-4-(3-fluorophenoxy)-5-methylsulfonylbenzoic acid gives N-diaminomethylene-2-ethyl-4-(3-fluorophenoxy)-5-methylsulfonylbenzamide;

2-ethyl-4-(4-fluorophenoxy)-5-methylsulfonylbenzoic acid gives N-diaminomethylene-2-ethyl-4-(4-fluorophenoxy)-5-methylsulfonylbenzamide;

2-ethyl-4-(2,4-difluorophenoxy)-5-methylsulfonylbenzoic acid gives N-diaminomethylene-2-ethyl-4-(2,4-difluorophenoxy)-5-methylsulfonylbenzamide;

2-ethyl-4-benzyloxy-5-methylsulfonylbenzoic acid gives N-diaminomethylene-2-ethyl-4-benzyloxy-5-methylsulfonylbenzamide;

2-ethyl-4-(3-methoxyphenoxy)-5-methylsulfonylbenzoic acid gives N-diaminomethylene-2-ethyl-4-(3-methoxyphenoxy)-5-methylsulfonylbenzamide;

2-ethyl-4-(4-methoxyphenoxy)-5-methylsulfonylbenzoic acid gives N-diaminomethylene-2-ethyl-4-(4-methoxyphenoxy)-5-methylsulfonylbenzamide;

2-ethyl-4-(2,4-dimethoxyphenoxy)-5-methylsulfonylbenzoic acid gives N-diaminomethylene-2-ethyl-4-(2,4-dimethoxyphenoxy)-5-methylsulfonylbenzamide;

2-ethyl-4-(2-methoxyphenoxy)-5-methylsulfonylbenzoic acid gives N-diaminomethylene-2-ethyl-4-(2-methoxyphenoxy)-5-methylsulfonylbenzamide;

2-ethyl-4-(3-trifluoromethylphenoxy)-5-methylsulfonylbenzoic acid gives N-diaminomethylene-2-ethyl-4-(3-trifluoromethylphenoxy)-5-methylsulfonylbenzamide;

2-ethyl-4-(4-trifluoromethylphenoxy)-5-methylsulfonylbenzoic acid gives N-diaminomethylene-2-ethyl-4-(4-trifluoromethylphenoxy)-5-methylsulfonylbenzamide;

2-ethyl-4-(2-trifluoromethylphenoxy)-5-methylsulfonylbenzoic acid gives N-diaminomethylene-2-ethyl-4-(2-trifluoromethylphenoxy)-5-methylsulfonylbenzamide;

2-ethyl-4-(3-methylphenoxy)-5-methylsulfonylbenzoic acid gives N-diaminomethylene-2-ethyl-4-(3-methylphenoxy)-5-methylsulfonylbenzamide;

2-ethyl-4-(4-methylphenoxy)-5-methylsulfonylbenzoic acid gives N-diaminomethylene-2-ethyl-4-(4-methylphenoxy)-5-methylsulfonylbenzamide;

2-ethyl-4-(2,4-dimethylphenoxy)-5-methylsulfonylbenzoic acid gives N-diaminomethylene-2-ethyl-4-(2,4-dimethylphenoxy)-5-methylsulfonylbenzamide;

2-ethyl-4-(2-methylphenoxy)-5-methylsulfonylbenzoic acid gives N-diaminomethylene-2-ethyl-4-(2-methylphenoxy)-5-methylsulfonylbenzamide.

EXAMPLE 7

600 mg of N-diaminomethylene-2-methyl-4-methoxy-5-methylsulfonylbenzamide (obtainable according to Ex. 2) are boiled for 3 hours in 80 ml of pyridine together with 1 g of pyridine hydrochloride. The mixture is cooled and evaporated, and the residue is worked up in the customary manner to give N-diaminomethylene-2-methyl-4-hydroxy-5-methylsulfonylbenzamide, m.p. >260°.

EXAMPLE 8

1.1 g of N-diaminomethylene-2-ethyl-4-benzyloxy-5-methylsulfonylbenzamide (obtainable according to Ex. 6) are dissolved in 30 ml of toluene and treated at room temperature for one hour with hydrogen gas (p=1 atm) under the catalytic action of 150 mg of Pd-carbon (Pd content 1%). The reaction mixture is then filtered, and customary working up gives N-diaminomethylene-2-ethyl-4-hyrdoxy-5-methylsulfonylbenzamide.

The following examples relate to pharmaceutical preparations:

EXAMPLE 9

Analogously to Example 3 by reaction of 1N methanesulfonate solution with a N-diaminomethylene-2-methyl-4-R-5-methylsulfonyl-benzamide the following methanesulfonates are obtained (R=substituent in 4-position as subsequently given):

N-diaminomethylene-2-methyl-4-ethoxy-5-methylsulfonyl-benzamide, methanesulfonate;

N-diaminomethylene-2-methyl-4-isopropoxy-5-methylsulfonyl-benzamide, methanesulfonate;
N-diaminomethylene-2-methyl-4-cyclopentoxy-5-methylsulfonyl-benzamide, methanesulfonate;
N-diaminomethylene-2-methyl-4-cycloheyloxy-5-methylsulfonyl-benzamide, methanesulfonate;
N-diaminomethylene-2-methyl-4-benzyloxy-5-methylsulfonyl-benzamide, methanesulfonate;
N-diaminomethylene-2-methyl-4-phenoxy-5-methylsulfonyl-benzamide, methanesulfonate, m.p. 260°–262°;
N-diaminomethylene-2-methyl-4-tert.-butoxy-5-methylsulfonyl-benzamide, methanesulfonate, m.p. 164°–167°;
N-diaminomethylene-2-methyl-4-(3-chlorphenoxy)-5-methylsulfonyl-benzamide, methanesulfonate, m.p. >144°;
N-diaminomethylene-2-methyl-4-hydroxy-5-methylsulfonyl-benzamide, methanesulfonate;
N-diaminomethylene-2-methyl-4-(4-chlorphenoxy)-5-methylsulfonyl-benzamide, methanesulfonate, m.p. >260°;
N-diaminomethylene-2-methyl-4-(2-chlorphenoxy)-5-methylsulfonyl-benzamide, methanesulfonate, m.p. 217°–219°;

EXAMPLE 10

Analogously to Example 1, reaction of methyl 2-methyl-4-(3-propen-1-yl)-5-methylsulfonyl-benzoate with guanidine gives N-diaminomethylene-2-methyl-4-(3-propen-1-yl)-5-methylsulfonyl-benzamide, m.p. 207°–209°.

The relating methanesulfonate is obtained analogously to Example 9, m.p. 187°–189°.

EXAMPLE A

Injection Vials

A solution of 100 g of an active compound of the formula I and 5 g of disodium hydrogen phosphate are adjusted to pH 6.5 in 3 l of double-distilled water using 2N hydrochloric acid, sterilized by filtration, filled into injection vials, lyophilized under sterile conditions and aseptically sealed. Each injection vial contains 5 mg of active compound.

EXAMPLE B

Suppositories

A mixture of 20 g of an active compound of the formula I is melted with 100 g of soya lecithin and 1400 g of cocoa butter, poured into molds and allowed to cool. Each suppository contains 20 mg of active compound.

EXAMPLE C

Solution

A solution of 1 g of an active compound of the formula I, 9.38 g of $NaH_2PO_4 \cdot 2 H_2O$, 28.48 g of $Na_2HPO_4 \cdot 12 H_2O$ and 0.1 g of benzalkonium chloride is prepared in 940 ml of double-distilled water. The solution is adjusted to pH 6.8, made up to 1 l and sterilized by irradiation. This solution can be used in the form of eye drops.

EXAMPLE D

Ointment 500 mg of an active compound of the formula I are mixed with 99.5 g of petroleum jelly under aseptic conditions.

EXAMPLE E

Tablets

A mixture of 1 kg of active compound of the formula I, 4 kg of lactose, 1.2 kg of potato starch, 0.2 kg of talc and 0.1 kg of magnesium stearate is compressed to give tablets in a customary manner such that each tablet contains 10 mg of active compound.

EXAMPLE F

Coated Tablets

Analogously to Example E, tablets are pressed which are then coated in a customary manner with a coating of sucrose, potato starch, talc, tragacanth and colorant.

EXAMPLE G

Capsules 2 kg of active compound of the formula I are filled into hard gelatin capsules in the customary manner such that each capsule contains 20 mg of the active compound.

EXAMPLE H

Ampoules

A solution of 1 kg of active compound of the formula I in 60 l of double-distilled water is sterile-filtered, filled into ampoules, lyophilized under sterile conditions and sterile-sealed. Each ampoule contains 10 mg of active compound.

The preceding examples can be repeated with similar success by substituting the generically or specifically described reactants and/or operating conditions of this invention for those used in the preceding examples.

From the foregoing description, One skilled in the art can easily ascertain the essential characteristics of this invention, and without departing from the spirit and scope thereof, can make various changes and modifications of the invention to adapt it to various usages and conditions.

We claim:

1. A benzoylguanidine compound of the formula I

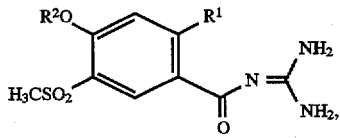

wherein
$R^1$ is methyl or ethyl and
$R^2$ is H, a straight-chain or branched $C_1$–$C_6$-alkyl- or $C_2$–$C_6$-alkenyl-radical, $C_3$–$C_7$-cycloalkyl, benzyl or phenyl which is unsubstituted or mono-, di- or trisubstituted by methyl, methoxy, amino, F, Cl, Br or $CF_3$, and their physiologically acceptable salts.

2. The compound:
   (a) N-diaminomethylene-2-methyl-4-phenoxy-5-methylsulfonylbenzamide;
   (b) N-diaminomethylene-2-ethyl-4-methoxy-5-methylsulfonylbenzamide;
   (c) N-diaminomethylene-2-methyl-4-ethoxy-5-methylsulfonylbenzamide;
   (d) N-diaminomethylene-2-methyl-4-(2-chloro-phenoxy)-5-methylsulfonylbenzamide; or
   (e) N-diaminomethylene-2-methyl-4-(4-chloro-phenoxy)-5-methylsulfonylbenzamide;

according to claim 1, or physiologically acceptable salts thereof.

3. A process for the preparation of the benzoylguanidine compounds of the formula I according to claim 1, and also their salts, which comprises reacting a compound of the formula II

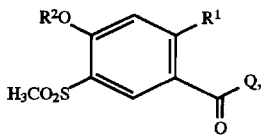

wherein $R^1$ and $R^2$ have the meanings indicated above,

Q is Cl, Br, OA, O—CO—A, —O—CO—Ph, OH or another reactive esterified OH group or leaving group which can be easily nucleophilically substituted and A is alkyl having 1–6 C atoms, with guanidine, or comprising reacting a benzoylguanidine of the formula III

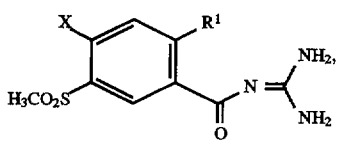

wherein $R^1$ has the meanings indicated above, and X is F, Cl, Br, I or another suitable leaving group, with an alcohol or phenol of the formula IV

     IV wherein $R^2$ has the meaning indicated, optionally after prior conversion to an alkoxide, or comprising reacting a phenol of the formula I wherein $R^2$=H and $R^1$ has the meaning indicated with a compound of the formula $R^2$—X wherein $R^2$ and X have the meanings indicated, or which comprises treating a compound which otherwise corresponds to the formula I, but which instead of one or more hydrogen atoms contains one or more reducible groups and/or one or more additional C-C and/or C-N bonds, with a reducing agent, or which comprises treating a compound which otherwise corresponds to the formula I, but which instead of one or more hydrogen atoms contains one or more solvolysable groups, with a solvolysing agent, or which comprises converting a base of the formula I into one of its salts by treating with an acid.

4. A process for the production of a pharmaceutical preparation, wherein a compound of the formula I according to claim 1 and/or one of its physiologically acceptable salts is brought into a suitable dose form together with at least one solid, liquid or semi-liquid excipient or auxiliary.

5. A pharmaceutical preparation, comprising at least one compound of the formula I according to claim 1 and/or one of its physiologically acceptable salts and a pharmaceutically acceptable carrier.

6. The compound of claim 1, wherein $R^2$ is methyl, ethyl, unsubstituted phenyl, phenyl monosubstituted by fluorine or chlorine, benzyl or cycloalkyl of 3, 5 or 6 carbon atoms.

7. A method for the treatment or preventive treatment of arrhythmias, angina pectoris and infarcts which comprises administering to a subject in need thereof a disease controlling effective amount of a compound of the formula I of claim 1 or a physiologically acceptable salt thereof.

8. A method for treating or preventing an illness indicated by activity of the cellular $Na^+/H^+$ antiporter which comprises administering to a patient a cellular $Na^+/H^+$ antiporter inhibiting effective amount of a compound according to formula I of claim 1 and/or one of its physiologically acceptable salts.

9. The method of claim 8, wherein the illness is cardiac arrhythmia, infarct, angina pectoris, an ischaemia of the nervous system, shock, hypertension, arteriosclerosis, diabetic late complications, oncoses, a fibrotic disorder or an organ hypertrophy or hyperplasia.

10. A method for inducing a cellular $Na^+/H^+$ antiporter inhibiting effect in a patient which comprises administering to the patient a cellular $Na^+/H^+$ antiporter inhibiting effective amount of a compound according to formula I of claim 1 and/or one of its physiologically acceptable salts.

11. A compound according to claim 1, wherein $R^1$ is methyl.

* * * * *